US008938308B2

(12) United States Patent
Meadows

(10) Patent No.: US 8,938,308 B2
(45) Date of Patent: *Jan. 20, 2015

(54) DEVICES AND METHODS FOR BRAIN STIMULATION

(71) Applicant: Boston Scientific Neuromodulation Corporation, Valencia, CA (US)

(72) Inventor: Paul M. Meadows, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/274,606

(22) Filed: May 9, 2014

(65) Prior Publication Data

US 2014/0249598 A1 Sep. 4, 2014

Related U.S. Application Data

(63) Continuation of application No. 13/943,175, filed on Jul. 16, 2013, now Pat. No. 8,755,905, which is a continuation of application No. 12/881,000, filed on Sep. 13, 2010, now Pat. No. 8,498,718, which is a continuation of application No. 11/030,546, filed on Jan. 5, 2005, now Pat. No. 7,809,446.

(51) Int. Cl.
*A61N 1/05* (2006.01)
*A61N 1/36* (2006.01)

(52) U.S. Cl.
CPC ............ *A61N 1/3606* (2013.01); *A61N 1/0529* (2013.01); *A61N 1/0534* (2013.01); *A61N 1/36017* (2013.01); *A61N 1/36021* (2013.01); *A61N 1/36071* (2013.01); *A61N 1/36003* (2013.01); *A61N 1/36025* (2013.01); *A61N 1/36082* (2013.01)
USPC .......................................................... 607/115

(58) Field of Classification Search
None
See application file for complete search history.

(56) References Cited

U.S. PATENT DOCUMENTS

| 4,350,159 A | 9/1982 | Gouda |
| 4,471,777 A | 9/1984 | McCorkle, Jr. |
| 4,565,200 A | 1/1986 | Cosman |
| 4,668,221 A | 5/1987 | Luther |
| 4,886,065 A | 12/1989 | Collins, Jr. |
| 4,931,056 A | 6/1990 | Ghajar et al. |
| 4,955,891 A | 9/1990 | Carol |
| 5,006,122 A | 4/1991 | Wyatt et al. |
| 5,114,424 A | 5/1992 | Hagen et al. |

(Continued)

FOREIGN PATENT DOCUMENTS

| EP | 1062973 A1 | 12/2000 |
| WO | 9936122 A1 | 7/1999 |

OTHER PUBLICATIONS

"System and Method for Selective Multi-Site Microeloectrode Recording," IP.com, IPCOM000016587D, Jul. 1, 2003.

(Continued)

*Primary Examiner* — Brian T Gedeon
(74) *Attorney, Agent, or Firm* — Lowe Graham Jones PLLC; Bruce E. Black

(57) ABSTRACT

A device for brain stimulation that includes n lead having a longitudinal surface; at least one stimulation electrode disposed along the longitudinal surface of the lead; and at least one recording electrode, separate from the at least one stimulation electrode, disposed along she longitudinal surface of the lead.

20 Claims, 4 Drawing Sheets

(56) References Cited

U.S. PATENT DOCUMENTS

| | | | |
|---|---|---|---|
| 5,116,345 | A | 5/1992 | Jewell et al. |
| 5,300,080 | A | 4/1994 | Clayman et al. |
| 5,303,704 | A | 4/1994 | Molacek et al. |
| 5,318,041 | A | 6/1994 | DuBois et al. |
| 5,330,485 | A | 7/1994 | Clayman et al. |
| 5,450,846 | A | 9/1995 | Goldreyer |
| 5,579,764 | A | 12/1996 | Goldreyer |
| 5,618,287 | A | 4/1997 | Fogarty et al. |
| 5,728,148 | A | 3/1998 | Bostrom et al. |
| 5,752,937 | A | 5/1998 | Otten et al. |
| 5,843,148 | A | 12/1998 | Gijsbers et al. |
| 5,913,882 | A | 6/1999 | King |
| 5,925,073 | A | 7/1999 | Chastain et al. |
| 5,978,713 | A | 11/1999 | Prutchi et al. |
| 6,011,996 | A | 1/2000 | Gielen et al. |
| 6,026,567 | A | 2/2000 | Swoyer et al. |
| 6,066,165 | A | 5/2000 | Racz |
| 6,181,971 | B1 | 1/2001 | Doan |
| 6,261,300 | B1 | 7/2001 | Carol et al. |
| 6,301,492 | B1 | 10/2001 | Zonenshayn |
| 6,343,226 | B1 | 1/2002 | Sunde et al. |
| 6,413,263 | B1 | 7/2002 | Lobdill et al. |
| 6,416,520 | B1 | 7/2002 | Kynast et al. |
| 6,456,869 | B1 | 9/2002 | Raylman et al. |
| 6,456,889 | B2 | 9/2002 | Pianca et al. |
| 6,510,347 | B2 | 1/2003 | Borkan |
| 6,529,774 | B1 | 3/2003 | Greene |
| 6,572,624 | B2 | 6/2003 | U et al. |
| 6,597,954 | B1 | 7/2003 | Pless et al. |
| 6,687,549 | B1 | 2/2004 | Helland et al. |
| 6,782,292 | B2 | 8/2004 | Whitehurst |
| 6,849,062 | B2 | 2/2005 | Kantor |
| 7,033,326 | B1 | 4/2006 | Pianca et al. |
| 7,177,701 | B1 | 2/2007 | Pianca |
| 7,212,867 | B2 | 5/2007 | Van Venrooij et al. |
| 7,783,359 | B2 | 8/2010 | Meadows |
| 7,809,446 | B2 | 10/2010 | Meadows |
| 8,498,718 | B2 | 7/2013 | Meadows |
| 8,571,665 | B2 | 10/2013 | Moffitt et al. |
| 2001/0027336 | A1 | 10/2001 | Gielen et al. |
| 2002/0151924 | A1 | 10/2002 | Shiber |
| 2004/0199235 | A1 | 10/2004 | Younis |
| 2005/0004637 | A1 | 1/2005 | Singhal et al. |
| 2005/0015130 | A1 | 1/2005 | Gill |
| 2008/0103572 | A1 | 5/2008 | Gerber |

OTHER PUBLICATIONS

"Universaly Instrument Guide and Surgical Insertion Tool for Stereotactic Frames," IP.com, IPCOM00011023D, Feb. 7, 2003.
Official Communication for U.S. Appl. No. 11/030,546 mailed Sep. 26, 2007.
Official Communication for U.S. Appl. No. 11/030,546 mailed Mar. 20, 2008.
Official Communication for U.S. Appl. No. 11/030,546 mailed May 21, 2008.
Official Communication for U.S. Appl. No. 11/030,546 mailed Jan. 21, 2009.
Official Communication for U.S. Appl. No. 11/030,546 mailed May 22, 2009.
Official Communication for U.S. Appl. No. 11/030,546 mailed Dec. 7, 2009.
Official Communication for U.S. Appl. No. 11/030,546 mailed Dec. 28, 2009.
Official Communication for U.S. Appl. No. 11/030,546 mailed Jun. 17, 2010.
Official Communication for U.S. Appl. No. 11/230,052 mailed Sep. 26, 2007.
Official Communication for U.S. Appl. No. 11/230,052 mailed Mar. 18, 2008.
Official Communication for U.S. Appl. No. 11/230,052 mailed May 27, 2008.
Official Communication for U.S. Appl. No. 11/230,052 mailed Sep. 30, 2008.
Official Communication for U.S. Appl. No. 11/230,052 mailed Jan. 29, 2009.
Official Communication for U.S. Appl. No. 11/230,052 mailed Jun. 1, 2009.
Official Communication for U.S. Appl. No. 11/230,052 mailed Aug. 12, 2009.
Official Communication for U.S. Appl. No. 11/230,052 mailed Dec. 28, 2009.
Official Communication for U.S. Appl. No. 11/230,052 mailed May 7, 2010.
Official Communication for U.S. Appl. No. 12/881,000 mailed Nov. 6, 2012.
Official Communication for U.S. Appl. No. 12/881,000 mailed Feb. 20, 2013.
Official Communication for U.S. Appl. No. 13/943,175 mailed Nov. 26, 2013.

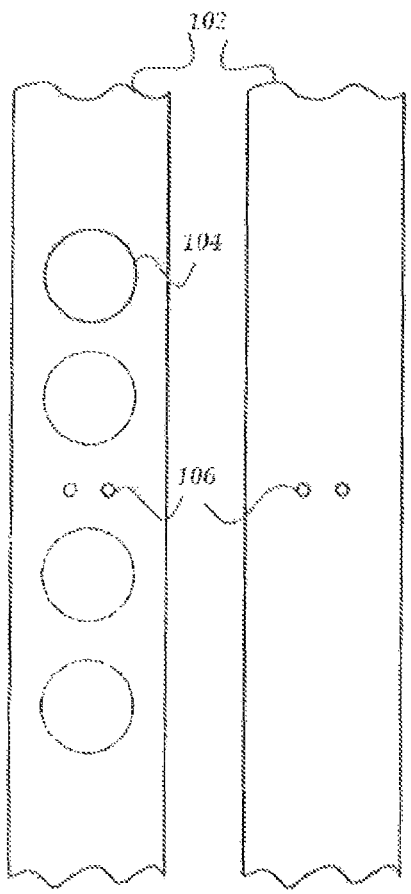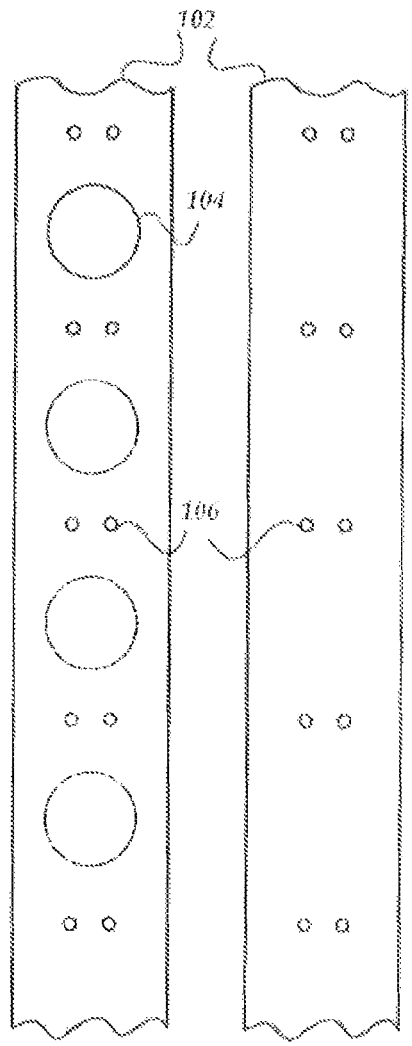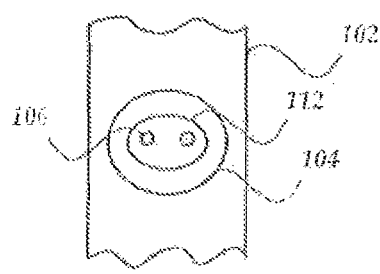
Figure 2A  Figure 2B
Figure 3A  Figure 3B
Figure 4

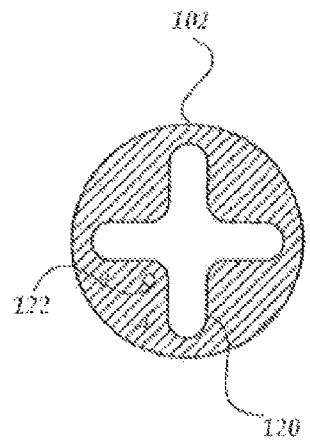
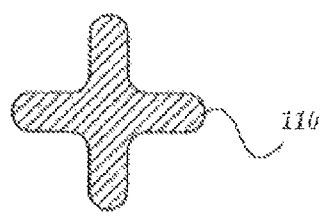
Figure 5A                Figure 5B
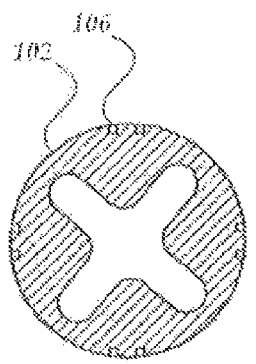
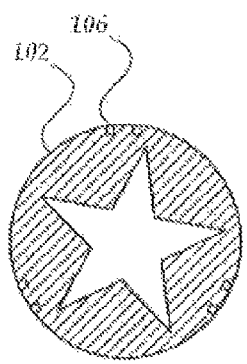
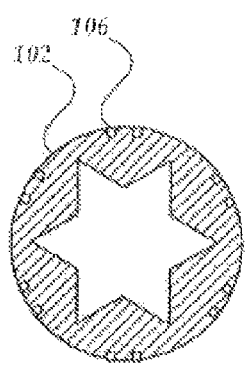
Figure 6A          Figure 6B          Figure 6C

DEVICES AND METHODS FOR BRAIN STIMULATION

CROSS-REFERENCE TO RELATED APPLICATION

This patent application is a continuation of allowed U.S. application Ser. No. 13/943,175 filed Jul. 16, 2013 which is a continuation of U.S. patent application Ser. No. 12/881,000 filed on Sep. 13, 2010, now U.S. Pat. No. 8,498,718, which is a continuation of U.S. patent application Ser. No. 11/030,546 tiled on Jan. 5, 2005, now U.S. Pat. No. 7,809,446, which is incorporated herein by reference.

FIELD

The invention is directed to devices and methods for brain stimulation including deep brain stimulation. In addition, the invention is directed to devices and method for brain stimulation using a lead with at least one recording electrode and at least one stimulating electrode.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons. To further refine the position, a recording lead with a recording electrode at or near the tip of the recording lead can be inserted into the brain of the patient to determine a more precise location. Typically, the recording lead is guided to the target location within the brain using a stereotactic frame and microdrive motor system.

As the recording lead is moved through the brain, the recording electrode is observed to determine when the recording electrode is near the target neurons. This observation may include activating the target neurons to generate electrical signals that can be received by the recording electrode. Once the position of the target neurons is determined, the recording lead can be removed and the stimulating lead inserted. The object of this removal of the recording lead and insertion of the stimulating lead is to attempt to precisely locate the target neurons. The precise insertion of the stimulating lead and positioning of the stimulating lead in the precise location indicated by the recording lead can be particularly difficult. In some instances, multiple insertions of the recording lead and stimulating lead may need to occur to properly position the stimulating electrode.

BRIEF SUMMARY

One embodiment is a device for brain stimulation that includes a lead having a longitudinal surface; at least one stimulation electrode disposed along the longitudinal surface of the lead; and at least one recording electrode, separate from the at least one stimulation electrode, disposed along the longitudinal surface of the lead.

Another embodiment is a device for brain stimulation that includes a lead having a circumference; and a set of recording electrodes disposed at intervals around the circumference of the lead.

Yet another embodiment is a device for brain stimulation that includes a lead defining a lumen having a non-circular lateral cross-section; and at least one electrode disposed on the lead.

A further embodiment is a method for brain stimulation. A lead is inserted into a cranium of a patient. The lead includes at least one stimulation electrode disposed along a longitudinal surface of the lead; and at least one recording electrode, separate from the at least one stimulation electrode, disposed along the longitudinal surface of the lead. Target neurons are identified using the at least one recording electrode. The target neurons are stimulated using the at least one stimulation electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A is a schematic side view of one embodiment of an electrode configuration for use with the lead of FIG. 1, according to the invention;

FIG. 2B is a schematic side view of one embodiment of an opposite side of the lead illustrated in FIG. 2A, according to the invention;

FIG. 3A is a schematic side view of another embodiment of an electrode configuration for use with the lead of FIG. 1, according to the invention;

FIG. 3B is a schematic side view of one embodiment of an opposite side of the lead illustrated in FIG. 3A, according to the invention;

FIG. 4 is a schematic side view of one embodiment of a recording electrode and stimulation electrode arrangement, according to the invention;

FIG. 5A is a schematic cross-sectional view of one embodiment of a lead with a cruciform lumen, according to the invention;

FIG. 5B is a schematic cross-sectional view of one embodiment of a stylet for use with the lead of FIG. 5A, according to the invention;

FIGS. 6A, 6B, and 6C are schematic cross-sectional views of three embodiments illustrating recording electrode arrangements arranged around the circumference of a lead, according to the invention.

DETAILED DESCRIPTION

The present invention is directed to the area of devices and methods for brain stimulation including deep brain stimulation. In addition, the invention is directed to devices and method for brain stimulation using a lead with at least one recording electrode and at least one stimulating electrode.

A lead for deep brain stimulation can include both recording and stimulation electrodes. This allows a practitioner to determine the position of the target neurons using the recording electrode(s) and then position the stimulation electrode(s) accordingly without removal of a recording lead and insertion of a stimulation lead. A lead can also include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Figure 1:
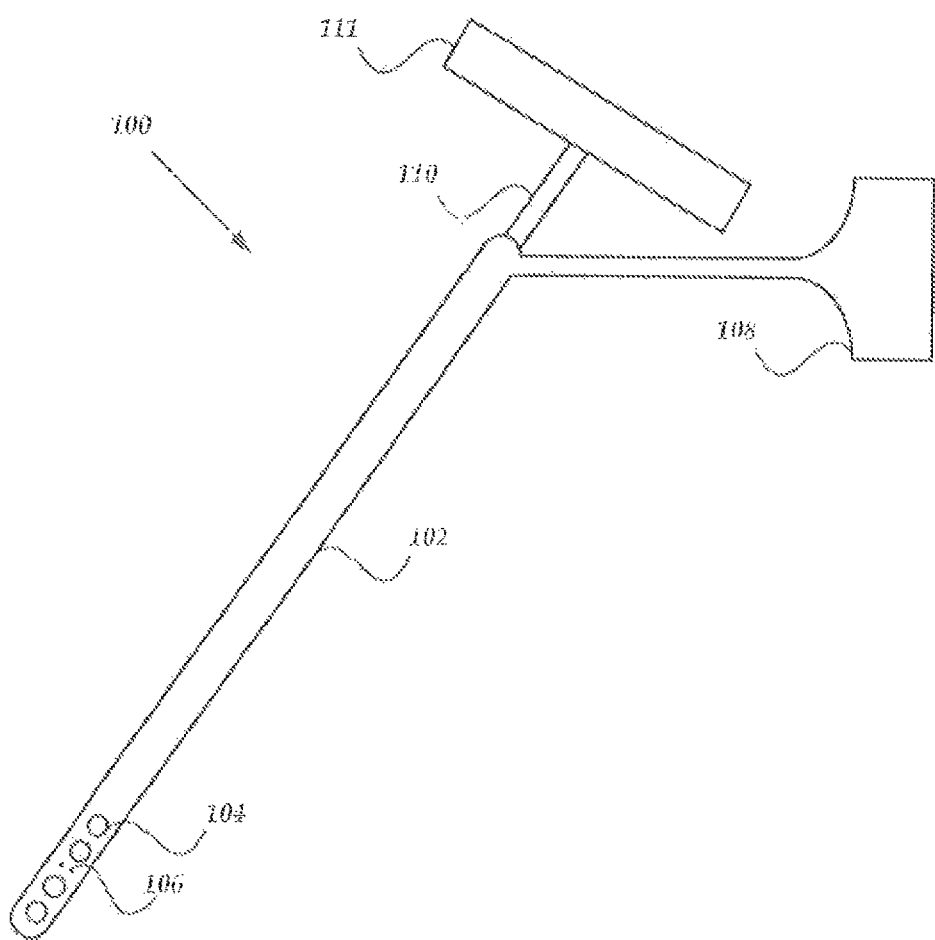
FIG. 1 is a schematic side view of one embodiment of a lead and stylet, according to the invention.

FIG. 1 illustrates one embodiment of a device 100 for brain stimulation. The device includes a lead 102, one or more stimulation electrodes 104, one or more recording electrodes 106, a connector 108 for connection of the electrodes to a control unit, and a stylet 110 for assisting in insertion and positioning of the lead in the patient's brain.

The lead 102 can be formed of a non-conducting material such as, for example, a polymeric material. Suitable polymeric materials include, for example, silicone rubber and polyethylene. Preferably, the lead is made using a biocompatible material. In at least some instances, the lead may be in contact, with body tissue for extended periods of time.

The lead often has a cross-sectional diameter of no more than 1.5 mm and may be in the range of 1 to 1.2 mm. The lead often has a length of at least 10 cm and the length of the lead may be in the range of 30 to 70 cm.

The lead typically defines a lumen 120 (see FIG. 5A) within the lead for the removable stylet 110. Use of a stylet can facilitate insertion of the lead into the cranium and brain tissue and facilitate positioning the lead to stimulate the target neurons. The stylet can provide rigidity to the lead during the insertion process.

The lumen can have any shape. In one embodiment, the lateral cross-sectional shape of the lumen is non-circular. For example, the lateral cross-sectional shape of the lumen can have an oval, square, rectangular, or, as illustrated in FIG. 5A, a cruciform shape. The stylet 110 will typically have a corresponding lateral cross-sectional shape. For example, a stylet 110 may have a cruciform shape as illustrated in FIG. 5B for use with the lead illustrated in FIG. 5A. The non-circular lateral cross-sectional shape can permit the practitioner to rotate the lead 102 by rotating the stylet 110. Because the lumen is non-circular, the stylet can not rotate within the lead and, therefore, rotation of the stylet results in rotation of the lead. A cruciform shaped lumen can be particularly useful, as opposed to an oval, square or rectangular lumen, if the shape of the lumen might be deformed by rotation of the stylet because the lead is not sufficiently rigid. Shapes similar to cruciform with multiple arms extending from a central cavity, such as an asterisk- or star-shaped lumen (see FIGS. 6B and 6C) and corresponding stylet, can be similarly useful.

The stylet 110 can be made of a rigid material. Examples of suitable materials include tungsten, stainless steel, or plastic. The stylet 110 may have a handle 111 to assist insertion into the lead, as well as rotation of the stylet and lead.

Conductors 122 (e.g., wires) that attach to or form the recording electrode(s) 106 and stimulation electrode(s) 104 also pass through the lead 102. These conductors may pass through the material of the lead as illustrated, for example, in one configuration for FIG. 5A, or through the lumen 120 or through a second lumen defined by the lead. The conductors 122 are presented at the connector 108 for coupling of the electrodes 104, 106 to a control unit (not shown). The control unit observes and records signals from the recording electrodes 106. The same or a different control unit can also he used to provide stimulation signals, often in the form of pulses, to the stimulation electrodes 104.

The lead 102 includes one or more recording electrodes 106 disposed along the longitudinal axis of the lead near a distal end of the lead. In at least some embodiments, the lead includes a plurality of recording electrodes. The recording electrodes can be made using a metal, alloy, conductive oxide, or other conductive material. Examples of suitable materials include platinum, iridium, platinum iridium alloy, stainless steel, titanium, or tungsten.

Any type of recording electrode can be used including monopolar recording electrodes, bipolar recording electrodes (as illustrated in FIGS. 1-4), and other multipolar recording electrodes. In at least some embodiments, bipolar or other multipolar recording electrodes are preferred because they can assist in finding nearby electrical signals, and disregard distant electrical signals, by observation of the differential between the signals from the two or more, closely-spaced electrodes.

Any type of recording electrode can be used including electrode pads or plates. A preferred recording electrode for at least some embodiments is a tip of a wire. This type of electrode can assist in more precise location of the target neurons because of the small surface area for detection of electrical signals. Such recording electrodes often have a diameter of no more than 100 μm or no more than 50 μm. The diameter may be in the range from, for example, 25 μm to 100 μm. In one embodiment, the recording electrodes 106 correspond to wire conductors 122 that extend out of the lead 102 and are then trimmed or ground down flush with the lead surface.

The lead 102 also includes one or more stimulation electrodes 104 arranged along the longitudinal axis of the lead near a distal end of the lead. In at least some embodiments, the lead includes a plurality of stimulation electrodes. A conductor 122 is attached to each stimulation electrode 104. The stimulation electrodes often have a surface area of at least 1 mm$^2$ or at least 5 mm$^2$. The surface area may be in the range from, for example, 1 mm$^2$ to 6 mm$^2$. A variety of shapes can be used for the stimulation electrodes including, for example, rings, circles, ovals, squares, rectangles, triangles, etc. In some embodiments, a stimulation electrode 104 forms a ring that fully or substantially encircles the lead 102. Preferably, however, the stimulation electrodes are not rings, but are instead discrete shapes disposed on one side of the lead. Ring electrodes typically stimulate neurons on all sides of the lead instead, of focusing on the target neurons that may face only a portion of the lead circumference.

The stimulation electrodes can be made using a metal, alloy, conductive oxide or other conductive material Examples of suitable materials include platinum, iridium, platinum iridium alloy, stainless steel, titanium, or tungsten. Preferably, the stimulation electrodes axe made of a material that is biocompatible and does not substantially corrode under expected operating conditions in the operating environment for the expected duration of use.

The arrangement of recording electrodes 106 and stimulation electrodes 104 on the lead 102 can facilitate detection and stimulation of target neurons. Some embodiments include a single recording electrode and a single stimulation electrode. Other embodiments, however, include two or more recording electrodes, two or more stimulation electrodes, or both.

FIG. 2A illustrates one embodiment of an electrode arrangement along the lead 102. In this embodiment, there are a plurality of stimulation electrodes 104 aligned along one side of the lead with a recording electrode 106 positioned in the center of the arrangement. In other embodiments, the recording electrode 106 can be positioned in any relationship relative to the array of stimulation electrodes including, for example, below or above all of the stimulation electrodes or between any two of the stimulation electrodes. When the target neurons have been discovered using the recording electrode, they can be stimulated using one or more of the stimulation electrodes. Optionally, the lead can be advanced or retreated to further align one or more of the stimulation electrodes with the target neurons.

FIG. 3A illustrates another embodiment of an electrode arrangement. In this arrangement, recording electrodes 106 are provided above and below each stimulation electrode 104 in an array of stimulation electrodes. Again, variations on this arrangement can be made. For example, recording electrodes may only be provided above and below, but not between, the array of stimulation electrodes. In another arrangement, the recording electrodes may be positioned only between the stimulation electrodes or only positioned between selected stimulation electrodes but not between others.

In other embodiments, one or more recording electrodes 106 may be provided within one or more of the stimulation electrodes 104. One example of such an arrangement is illustrated in FIG. 4. In this arrangement, the stimulation electrode 104 surrounds the recording electrode 106. There is a non-conducting region 112 separating the stimulation electrode 104 and the recording electrode 106. This electrode arrangement may be advantageous when the recording electrode identifies the target neurons because the stimulation electrode is already in place to stimulate the target neurons. In addition, during operation of the lead, the recording electrodes can be periodically checked to determine whether the lead is still correctly positioned to stimulate the target neurons without needing to move the lead to align the recording electrodes with the target neurons. In these embodiments, recording electrode(s) can be positioned within each stimulation electrode or within a select number of stimulation electrodes or even within only one of the stimulation electrodes.

In at least some embodiments, recording electrodes 106 are arranged at various positions around the lateral circumference of the lead 102. Examples of such arrangements are illustrated in the cross-sectional views of FIGS. 6A, 6B, and 6C. In these arrangements, the recording electrodes are positioned in irregular or, preferably, regular intervals around the lead. For example, in FIG. 6A, the recording electrodes 106 are positioned around the lead with about 90° separation between neighboring recording electrodes. In FIG. 6B, the recording electrodes 106 are positioned around the lead with about 120° separation between neighboring recording electrodes. In FIG. 6C, the recording electrodes 106 are positioned around the lead with about 60° separation between neighboring recording electrodes. It will be recognized that other arrangements can be made including, for example, arrangements with 180° or 72° separation between recording electrodes 106.

Positioning the recording electrodes 106 around the lead 102 in this manner can assist in determining the position of the target neurons because the recording electrodes can sample the brain tissue around the lead without rotating the lead. FIGS. 2B and 3B illustrate embodiments with recording electrodes 106 on the opposite side of the lead from the stimulation/recording electrode arrangements illustrated in FIGS. 2A and 3A, respectively.

Stimulation electrodes 104 can be positioned around the circumference of the lead 102 in a similar manner as that described for the recording electrodes. In at least some embodiments, however, stimulation electrode(s) 104 are positioned only along one side of the lead 102 and one or more sets of recording electrodes 106 are arrayed around the lateral circumference of the lead. Sets of recording electrodes can be displaced from each other longitudinally along the lead (e.g., the arrangement illustrated in FIGS. 3A and 3B). Optionally, one or more of the recording electrodes can be positioned within one or more of the stimulation electrode using an arrangement such as that illustrated in FIG. 4.

The recording electrodes 106 can be used to determine the site of the target neurons and then the lead can then be rotated, if necessary when the recording electrode is not one of those aligned with the stimulation electrode(s), and advanced or retreated, if necessary or desired, to align the stimulation electrode(s) with the target neurons. Rotation of the lead can be facilitated using a stylet and lead with non-circular lumen such as, for example, those illustrated in FIGS. 5A and 5B. The stylet or the proximal end of the lead may include an alignment marker to indicate where stimulation electrodes are provided along the lead.

Figure 7:
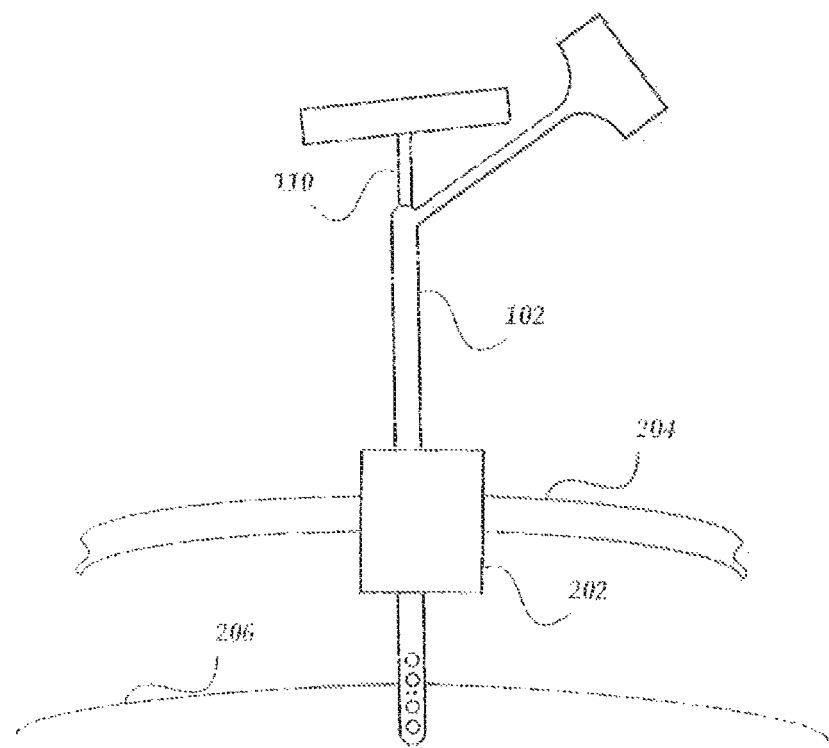
FIG. 7 is a schematic side view of a lead and associated hardware for insertion into a cranium, according to the invention.

In one example of operation of the lead illustrated in FIG. 7, access to the desired position in the brain can be accomplished by drilling a hole in the patient's skull or cranium 206 with a cranial drill (commonly referred to as a burr), and coagulating and incising the dura mater, or brain covering. The lead 102 can be inserted into the cranium and brain tissue with the assistance of the stylet 110. The lead can be guided to the target location within the brain using, for example, a stereotactic frame 204 and a microdrive motor system 202. The recording electrode(s) 106 can be observed using a control unit (not shown) attached to the conductors 122 exposed at the connector 108 to identify the target neurons. Once identified, the lead can be rotated, if necessary, and advanced or retreated, if necessary, to align the stimulation electrode(s) with the target neurons. The stimulation electrodes can then be activated to provide the desired stimulation to the target neurons and the stylet can then be removed.

In some embodiments, the microdrive motor system 202 can be fully or partially automatic. For example, the microdrive motor system 202 can perform one or more actions on the lead 102 in response to the signals from the recording electrode(s) 106, stimulation electrode(s) 104, or both. The microdrive motor system may be configured to perform one or more the following actions (alone or in combination): rotate the lead, insert the lead, or retract the lead. In one embodiment, the microdrive motor system, can rotate the lead to position the stimulation electrode(s) in the position of the recording electrode(s) that detect the target neurons. In another embodiment, the microdrive motor system can rotate the bad partially and the recording electrode(s) can then be observed, in the new position to iteratively determine the best position for the stimulation electrode(s). For example, if recording electrodes are positioned every 90° around the lead, the initial rotation of the lead can be less than 90° (e.g., 30° or 45°) and the recording electrodes can again be observed to more accurately identify the location of the target neurons.

In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can he used to observe the muscle and indicate changes in tremor frequency or amplitude in response to stimulation of neurons. Alternatively, the patient or clinician may observe the muscle and provide feedback.

The above specification, examples and data provide a description of the manufacture and use of the composition of the invention. Since many embodiments of the invention can be made without departing from the spirit and scope of the invention, the invention also resides in the claims hereinafter appended.

The invention claimed is:

1. A device for electrical stimulation, comprising:
a lead having a longitudinal surface and a circumference;
a plurality of first electrodes disposed along the longitudinal surface of the lead, each first electrode being a ring; and
a plurality of second electrodes separate from the first electrodes, wherein the second electrodes are divided into a plurality of sets, each set comprising at least two second electrodes disposed at intervals around the circumference of the lead at a same longitudinal position along the lead, wherein at least one of the first electrodes is separated from all other first electrodes by at least one set of second electrodes.

2. The device of claim 1, wherein each set of second electrodes is separated from other sets of second electrodes by at least one of the first electrodes.

3. The device of claim 1, wherein the second electrodes of each set are disposed at regular intervals around the circumference of the lead.

4. The device of claim 1, wherein at least one of the sets of second electrodes comprises four second electrodes disposed around the circumference of the lead at 90° intervals.

5. The device of claim 1, wherein at least one of the sets of second electrodes comprises three second electrodes disposed around the circumference of the lead at 120° intervals.

6. The device of claim 1, wherein the lead defines a lumen having a non-circular lateral cross-section extending longitudinally through at least a portion of the lead.

7. The device of claim 6, wherein the lumen has a cruciform lateral cross-section.

8. The device of claim 6, wherein the lumen has a star-shaped lateral cross-section.

9. The device of claim 6, further comprising a stylet having a lateral cross-section corresponding to the lateral cross-section of the lumen.

10. The device of claim 1, further comprising a microdrive motor system coupled to the lead to facilitate positioning of the lead in a brain of a patient.

11. The device of claim 10, wherein the microdrive motor system is configured and arranged to be responsive to signals from at least one of the first or second electrodes.

12. The device of claim 1, wherein each set of second electrodes comprises at least three second electrodes.

13. A device for electrical stimulation, comprising:
a lead having a longitudinal surface and a circumference, wherein the lead is configured and arranged for implantation in a patient;
a plurality of stimulation electrodes disposed along the longitudinal surface of the lead and configured and arranged for stimulation of patient tissue, each stimulation electrode having a square or rectangular shape; and
a plurality of sets of recording electrodes separate from the at least one stimulation electrode each set of recording electrodes comprises a plurality of recording electrodes disposed at intervals around the circumference of the lead at a same longitudinal position along the lead, wherein at least one of the stimulation electrodes is separated from all other stimulation electrodes by at least one set of recording electrodes.

14. The device of claim 13, wherein at least one of the recording electrodes is surrounded by a one of the stimulation electrodes.

15. The device of claim 13, wherein each set of second electrodes is separated from other sets of second electrodes by at least one of the first electrodes.

16. A method for brain stimulation, the method comprising:
inserting the lead of the device of claim 1 into a patient;
identifying target neurons using the second electrodes; and
stimulating the target neurons using at least one of the first electrodes.

17. The method of claim 16, further comprising inserting a stylet into the lead to assist in inserting the lead into the patient.

18. The method of claim 17, where the lead defines a lumen having a non-circular lateral cross-section extending longitudinally through at least a portion of the lead and the stylet has a corresponding non-circular lateral cross-section, the method further comprising rotating the lead by rotating the stylet.

19. The method of claim 16, wherein inserting the lead comprising using a microdrive motor system coupled to the lead to insert and position of the lead in the patient.

20. The method of claim 19, wherein using a microdrive motor system comprises rotating the lead using the microdrive motor system in response to signals from at least one of the first or second electrodes.

* * * * *